(12) United States Patent
Kalnes et al.

(10) Patent No.: US 10,369,556 B2
(45) Date of Patent: Aug. 6, 2019

(54) INTEGRATED PROCESS FOR GASOLINE PRODUCTION

(71) Applicant: UOP LLC, Des Plaines, IL (US)

(72) Inventors: Tom N. Kalnes, LaGrange, IL (US); Stuart Smith, Lake Zurich, IL (US); Douglas A. Nafis, Mt. Prospect, IL (US); Alakananda Bhattacharyya, Glen Ellyn, IL (US); Bryan K. Glover, Algonquin, IL (US); Susie C. Martins, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 103 days.

(21) Appl. No.: 14/567,804

(22) Filed: Dec. 11, 2014

(65) Prior Publication Data

US 2016/0168054 A1    Jun. 16, 2016

(51) Int. Cl.
| | |
|---|---|
| *C07C 6/00* | (2006.01) |
| *B01J 31/00* | (2006.01) |
| *C07C 6/10* | (2006.01) |
| *C10G 29/20* | (2006.01) |
| *B01J 31/02* | (2006.01) |

(52) U.S. Cl.
CPC .............. *B01J 31/00* (2013.01); *C07C 6/10* (2013.01); *C10G 29/205* (2013.01); *B01J 31/0288* (2013.01); *B01J 31/0298* (2013.01); *B01J 2231/32* (2013.01); *C10G 2400/02* (2013.01)

(58) Field of Classification Search
CPC ................................... B01J 31/00; C07C 2/54

USPC ................................................... 585/310, 312
See application file for complete search history.

(56) References Cited

U.S. PATENT DOCUMENTS

| | | | |
|---|---|---|---|
| 3,718,576 A | | 2/1973 | Hughes et al. |
| 3,812,199 A | * | 5/1974 | Lucki ....................... B01J 29/04 |
| | | | 208/120.01 |
| 3,953,537 A | | 4/1976 | Chloupek et al. |
| | | | (Continued) |

FOREIGN PATENT DOCUMENTS

CN          101892071 A      11/2010

*Primary Examiner* — Philip Y Louie
*Assistant Examiner* — Aaron W Pierpont

(57) ABSTRACT

An integrated process for gasoline production is described. The process includes introducing a feed comprising n-$C_5$ hydrocarbons into a disproportionation reaction zone in the presence of a disproportionation catalyst to form a disproportionation mixture comprising iso-$C_4$ and $C_{6+}$ disproportionation products and unreacted n-$C_5$ hydrocarbons. An iso-$C_4$ hydrocarbon stream and an olefin feed are introduced into an alkylation reaction zone in the presence of an alkylation catalyst to produce an alkylation mixture comprising alkylate and unreacted iso-$C_4$ paraffins. The disproportionation mixture and the alkylation mixture are combined, and the combined mixture is separated into at least a stream comprising the alkylate product, an iso-$C_4$ stream, and an unreacted n-$C_5$ hydrocarbon stream. The iso-$C_4$ stream is recycled to the alkylation reaction zone, and the unreacted n-$C_5$ hydrocarbon stream is recycled to the disproportionation reaction zone. The stream comprising the alkylate product is recovered.

14 Claims, 3 Drawing Sheets

(56) References Cited

U.S. PATENT DOCUMENTS

| | | | | |
|---|---|---|---|---|
| 4,383,977 A | * | 5/1983 | Hutson, Jr. | C07C 2/62 422/208 |
| 5,414,184 A | * | 5/1995 | Wu | C07C 6/10 585/708 |
| 5,489,727 A | * | 2/1996 | Randolph | C07C 6/10 585/702 |
| 6,423,880 B1 | * | 7/2002 | Randolph | C07C 6/10 585/310 |
| 6,573,416 B1 | | 6/2003 | Randolph | |
| 2002/0169071 A1 | * | 11/2002 | Sauvage | B01J 31/0295 502/150 |
| 2005/0033102 A1 | * | 2/2005 | Randolph | B01J 31/0294 585/708 |
| 2005/0131264 A1 | * | 6/2005 | Randolph | C07C 6/10 585/708 |
| 2009/0170688 A1 | * | 7/2009 | Chang | B01J 31/40 502/32 |
| 2010/0025292 A1 | * | 2/2010 | Hommeltoft | C10G 57/005 208/95 |
| 2016/0159710 A1 | * | 6/2016 | Smith | C07C 6/10 585/708 |

* cited by examiner

INTEGRATED PROCESS FOR GASOLINE PRODUCTION

BACKGROUND OF THE INVENTION

The use of catalytic alkylation processes to produce branched hydrocarbons having properties that are suitable for use as gasoline blending components is well known in the art. Generally, the alkylation of olefins, such as butenes, by isoparaffins, such as isobutane, is accomplished by contacting the reactants with an acid catalyst to form a reaction mixture, settling said mixture to separate the catalyst from the hydrocarbons, and further separating the hydrocarbons, for example, by fractionation, to recover the alkylation reaction product. Normally, the alkylation reaction product is referred to as "alkylate", and preferably contains hydrocarbons having 7-9 carbon atoms. In order to have the highest quality gasoline blending stock, it is preferred that hydrocarbons formed in the alkylation process be highly branched.

Due to the increased use of shale crude and tar sands, refiners must now accommodate a growing amount of normal paraffins, such as n-butanes and n-pentanes in the feedstock. Finally, some refineries are trying to manage an increasing amount of light olefin byproducts, such as propylene, produced in existing fluid catalytic cracking (FCC) units.

There is a need for a more flexible process that can accept these feeds without requiring additional isobutane from an external source.

SUMMARY OF THE INVENTION

One aspect of the invention is an integrated process for gasoline production. In one embodiment, the process includes introducing a feed comprising n-$C_5$ hydrocarbons to a disproportionation reaction zone in the presence of a disproportionation catalyst under disproportionation reaction conditions to form a disproportionation mixture comprising iso-$C_4$ and $C_{6+}$ disproportionation products and unreacted n-$C_5$ hydrocarbons. An iso-$C_4$ hydrocarbon stream and an olefin feed stream comprising at least one of ethylene, propylene, and butenes are introduced into an alkylation reaction zone in the presence of an alkylation catalyst under alkylation reaction conditions to produce an alkylation mixture comprising alkylate and unreacted iso-$C_4$ paraffins. The disproportionation mixture and the alkylation mixture are combined to form a combined mixture. The combined mixture is separated into at least a stream comprising the alkylate product, an iso-$C_4$ stream comprising the iso-$C_4$ disproportionation product and the unreacted iso-$C_4$, and a stream comprising the unreacted n-$C_5$ hydrocarbons. The iso-$C_4$ stream is recycled to the alkylation reaction zone wherein the iso-$C_4$ stream comprises the iso-$C_4$ hydrocarbon stream, and the stream comprising unreacted n-$C_5$ hydrocarbons is recycled to the disproportionation reaction zone. The stream comprising the alkylate product is recovered.

DETAILED DESCRIPTION OF THE INVENTION

Figure 1:
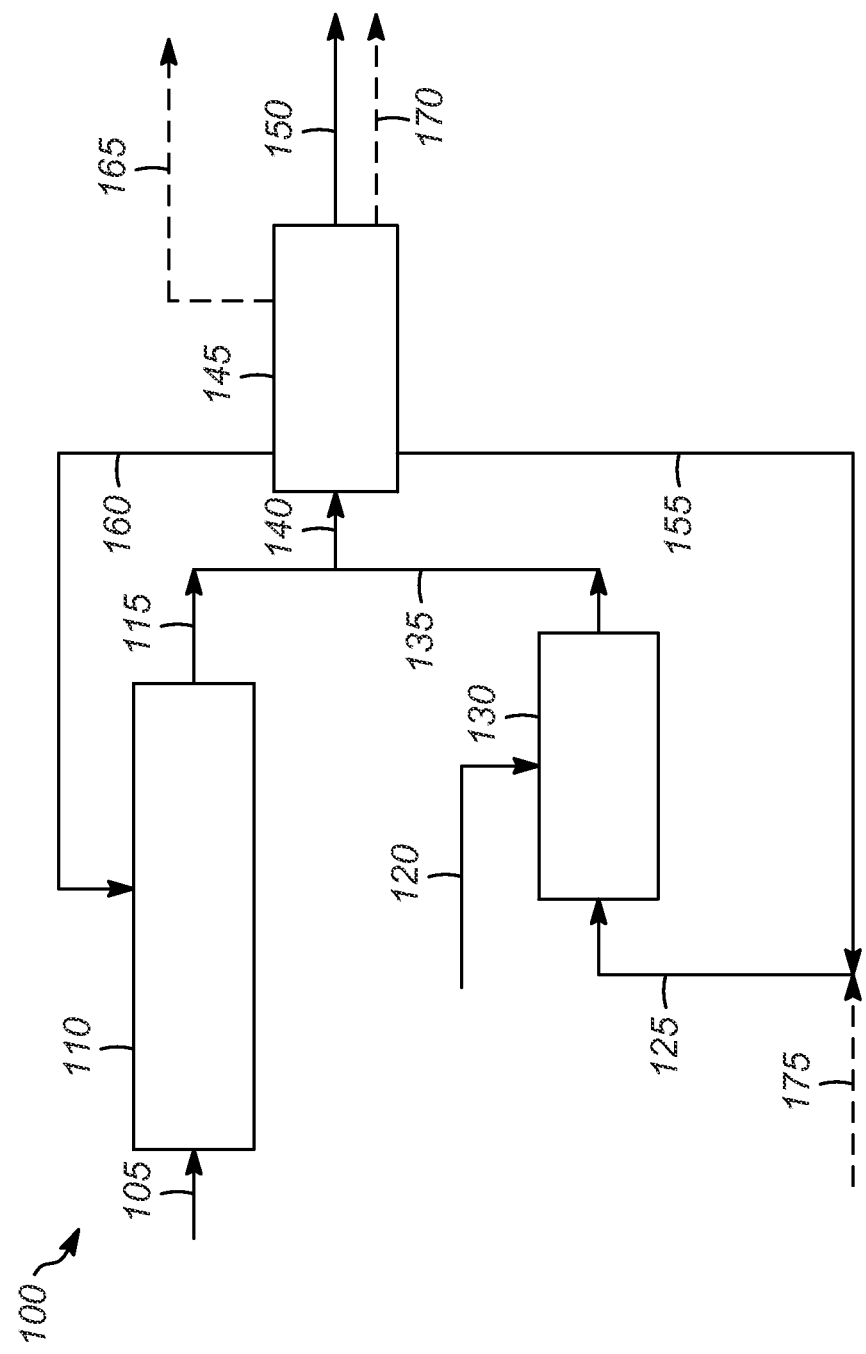
FIG. 1 is an illustration of one embodiment of a process according to the present invention.

By integrating a process for converting n-$C_5$ and optionally n-$C_4$ to i$C_{4-}$ and $C_{6+}$ products with an acid catalyzed alkylation process using iso-$C_4$, it is possible to increase conversion of lower value feedstocks to higher value gasoline blendstocks.

In the integrated process, n-$C_5$ and optionally n-$C_4$ are routed to a catalytic disproportionation reaction zone where they are converted to iso-$C_4$ and $C_{6+}$ isoparaffin-rich co-products. In the alkylation reaction zone, iso-$C_4$ from the disproportionation reaction is routed to the alkylation reaction zone and reacted with refinery propylene and butenes to produce alkylate product. The co-products of this reaction may include additional light naphtha ($C_5$ and $C_6$), $C_{9+}$ compounds, and lighter paraffins.

The effluents from the disproportionation reaction zone and the alkylation reaction zone are combined, and the combined stream is separated into two or more streams in a product separation zone. Unconverted n-$C_5$ and optionally n-$C_4$ and i-$C_5$ are recovered as liquids (typically in a single stream) and recycled back to the disproportionation reaction zone to increase conversion. Unconverted iso-$C_4$ and/or olefins are recycled to the alkylation reaction zone. One or more products streams are recovered. The product stream(s) can include one or more of an alkylate stream, and a $C_{6+}$ isoparaffin-rich stream. A product stream comprising the alkylate and the $C_{6+}$ isoparaffins can be recovered, if desired.

The integrated process allows conversion of excess n-$C_5$ and optionally n-$C_4$ in the summer months to lower RVP gasoline. It can allow the refinery to avoid purchasing iso-$C_4$ when the alkylation capacity is limited by iso-$C_4$ availability. In addition, it can expand the alkylation process by allowing the processing of propylene-rich feed from fluid catalytic cracking (FCC) reaction zones because of the presence of the disproportionation reaction zone.

The process also involves the in situ production of additional iso-$C_4$, which will allow greater utilization of refinery propylene in the production of high octane, low Reid Vapor Pressure (RVP) alkylate.

By combining the disproportionation and alkylation effluent and separating the combined effluent in a shared separation zone, the capital cost of the system is reduced. The shared equipment includes, but is not limited to, vapor-liquid and liquid-liquid separators, adsorbent beds for removing acidic impurities such as HF, HCl, or $H_2SO_4$, neutralization equipment, and distillation equipment (e.g., columns, reboilers, condensers, pumps, and the like).

The process also allows the products to be routed directly to the optimum reactor for maximizing yield and product quality. For example, iso-$C_4$ generated in the disproportionation reaction zone is combined with the unreacted iso-$C_4$ from the alkylation zone and recycled to the alkylation reaction zone. Similarly, any n-$C_5$ generated in the alkylation reaction zone can be recycled to the disproportionation reaction zone.

Another feature of the process is the composition of the gasoline product. In some embodiments, it will contain $C_{6+}$ isoparaffins from the disproportionation reaction zone in addition to alkylate from the alkylation reaction zone. This expanded product increases gasoline yield.

The catalyst for the alkylation reaction and/or the disproportionation reaction can be a solid acid catalyst or a liquid acid catalyst, such as hydrofluoric acid, sulfuric acid, and ionic liquids.

In some embodiments, when an ionic liquid is used, there can be a shared ionic liquid make-up source and regeneration zone.

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1$, $C_2$, $C_3$ ... $C_n$ where "n" represents the number of carbon atoms in the one or more hydrocarbon molecules. Additionally, characterizing a stream as, e.g., an "olefin stream" can mean a stream including or rich in at least one olefin.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and optimally about 70%, by mole or by weight, of a compound or class of compounds in a feed, an effluent, or a stream.

As used herein, the term "substantially" can mean an amount of at least generally about 80%, preferably about 90%, and optimally about 99%, by mole or by weight, of a compound or class of compounds in a feed, an effluent, or a stream.

As used herein, the term "vapor" can mean a gas or a dispersion that may include or consist of one or more hydrocarbons.

As used herein, the term "vaporization" can mean using at least one of heat and pressure to change at least a portion of a liquid to a gas optionally forming a dispersion, such as a gas entraining at least one of liquid and solid particles.

As used herein, the term "communicating" may mean two objects capable of receiving, directly or indirectly, a substance transmitted from one to the other.

As used herein, the term "hydrogen fluoride" can include at least one of a hydrogen fluoride or a hydrofluoric acid. Generally, a hydrofluoric acid is a solution of a hydrogen fluoride in water, where the hydrogen fluoride can disassociate and may form ions of $H_3O^+$, $H^+$, $FHF^-$, and $F^-$. The term includes anhydrous hydrogen fluoride.

As used herein, the term "about" means within 10% of the value, or within 5%, or within 1%.

As depicted, process flow lines in the figures can be referred to as lines, pipes, spargers, feeds, effluents, or streams. Particularly, a line, a sparger, or a pipe can contain one or more feeds, effluents, or streams, and one or more feeds, effluents, and streams can be contained by a line, a sparger, or a pipe. Generally, a sparger is a pipe forming a plurality of holes to improve dispersing of material from inside the pipe.

As illustrated in the process 100 shown in FIG. 1, a paraffin feed 105 comprising n-$C_5$ and optionally n-$C_4$ is introduced into disproportionation reaction zone 110.

The disproportionation of paraffins involves reacting two moles of hydrocarbon to form one mole each of two different products, one having a carbon count greater than the starting material and the other having a carbon count less than the starting material. The total number of moles in the system remains the same throughout the process, but the products have different carbon counts from the reactants. Additional secondary disproportionation-type reactions can occur in which two hydrocarbons having different carbon numbers react to form two different hydrocarbons having different carbon numbers from those of the feed (e.g., pentane and octane reacting to form hexane and heptanes or pentane and hexane reacting to form butane and heptane). For a feed of $C_x$, the disproportionation products include $C_x^+$ hydrocarbons and $C_x^-$ hydrocarbons.

The feed comprising n-$C_5$ and optionally n-$C_4$ can be obtained from natural gas liquids (NGLs), liquefied petroleum gas (LPGs), light straight-run naphtha, light naphtha, light natural gasoline, light reformate, light raffinate from aromatics extraction, light cracked naphtha, butanes, normal-butane concentrate, field butanes, and the like.

The disproportionation catalyst can be any suitable liquid or solid disproportionation catalyst, including, but not limited to, hydrofluoric acid (HF), sulfuric acid ($H_2SO_4$), fluorosulfonic acids, acidic ionic liquids, halides of Group III metals, zeolites, alumina, aluminosilicates, sulfated zirconias, and solid acid catalysts.

Typical disproportionation operating conditions include a temperature in the range of about 10° C. to about 300° C., or about 50° C. to about 300° C., a pressure in the range of about 0.1 MPa (g) to about 13.8 MPa (g), and a liquid hourly space velocity (LHSV) in the range of about 0.1 hr$^{-1}$ to about 1000 hr$^{-1}$, depending on the catalyst used. Disproportionation processes are described in U.S. Pat. Nos. 6,573,416, and 6,423,880, for example.

One suitable process and catalyst are described in application Ser. No. 4,562,390, entitled DISPROPORTIONATION OF HYDROCARBONS USING SOLID ACID CATALYSTS, filed Dec. 5, 2014, which is incorporated herein by reference. The catalyst comprises a refractory inorganic oxide having a metal halide dispersed thereon. There can optionally be a Group VIII metal component dispersed thereon. The reaction takes place in the presence of hydrogen and a chloride promoter. Suitable disproportionation reaction conditions for this catalyst include a temperature in the range of about 100° C. to about 300° C. The pressure is generally in the range of about 0 MPa (g) to about 13.8 MPa (g). The liquid hourly space velocity (LHSV) is generally in the range of about 0.25 hr$^{-1}$ to about 10 hr$^{-1}$. The mole ratio of hydrogen to hydrocarbon feed is in the range of greater than 0:1 to about 2:1, or 0:1 to about 1.5:1, or 0:1 to about 0.75:1, or 0:1 to about 0.5:1, or 0:1 to about 0.3:1, or 0:1 to about 0.1:1, or 0:1 to about 0.05:1, or about 0:1 to about 0.02:1, or 0:1 to about 0.01:1, or 0.01:1 to about 0.05:1. The chloride concentration of the added chloride promoter is typically in the range of greater than 0 to about 5000 ppm, and it typically ranges from about 100 ppm to about 5000 ppm, or about 200 ppm to about 5000 ppm, or about 400 ppm to about 5000 ppm, or about 600 ppm to about 5000 ppm, or about 800 ppm to about 5000 ppm, or about 1000 ppm to about 5000 ppm, or about 1200 ppm to about 5000 ppm, or about 1400 ppm to about 5000 ppm, or about 1600 ppm to about 5000 ppm. The mole ratio of hydrogen to chloride from the added chloride promoter is in the range of greater than 0:1 to about 5000:1, or 0:1 to about 2500:1, or 0:1 to about 1000:1, or 0:1 to about 750:1, or 0:1 to about 500:1, or 0:1 to about 250:1, or 0:1 to about 225:1, or 0:1 to about 200:1, or 0:1 to about 175:1, or 0:1 to about 150:1, or 0:1 to about 125:1, or 0:1 to about 100:1, or 0:1 to about 75:1, or 0:1 to about 50:1, or 0:1 to about 25:1, or 0:1 to about 15:1, or 0:1 to about 5:1, or 1:1 to about 10:1, or about 1:1 to 5:1.

The disproportionation reaction produces a disproportionation reaction mixture typically including $C_{3-}$, iso-$C_4$ and $C_{6+}$ disproportionation products, and unreacted n-$C_5$ and optionally n-$C_4$ paraffins. There will also be some isomerization of the n-$C_5$ and n-$C_4$ (if present) to iso-$C_5$ and iso-$C_4$.

The disproportionation effluent 115 contains the disproportionation products, unreacted feed, and any isomerization products.

An olefin feed stream 120 comprising at least one of ethylene, propylene, and butenes and an iso-$C_4$ stream 125 are introduced into the alkylation reaction zone 130. The olefin feed stream 120 can be obtained from an FCC unit, for example.

The olefins are alkylated by the iso-$C_4$ for production of high octane alkylate hydrocarbons boiling in the gasoline range and which are suitable for use in gasoline motor fuel. The alkylate hydrocarbon product comprises a major portion of highly branched high-octane aliphatic hydrocarbons having at least seven carbon atoms and less than 10 carbon atoms.

In order to improve selectivity of the alkylation reaction toward the production of the desirable highly branched aliphatic hydrocarbons having seven or more carbon atoms, a substantial stoichiometric excess of isoparaffin hydrocarbons is desirable in the reaction zone. In the alkylation process of the present invention, employing isoparaffins to olefin molar ratios in typically in excess of about 1:1, usually about 4:1 to about 100:1, or about 4:1 to about 70:1, or about 2:1 to about 25:1, or about 5:1 to about 20:1. Generally, the greater the isoparaffins to olefin ratio in an alkylation reaction, the better the results in alkylate quality.

Typically, the alkylation catalyst can include hydrogen fluoride, a sulfuric acid, a hydrofluoric acid, fluorosulfonic acids, a phosphoric acid, a metal halide (typically in conjunction with a Brønsted acid co-catalyst), or other suitable alkylation catalyst.

Alkylation reaction temperatures are typically in the range of from about 5° C. to about 150° C. Lower temperatures favor alkylation reaction of isoparaffins with olefins over competing olefin side reactions such as oligomerization and polymerization. However, overall reaction rates decrease with decreasing temperatures. Temperatures within the given range, and preferably in the range of from about 30° C. to about 130° C., provide good selectivity for alkylation of isoparaffins with olefins at commercially attractive reaction rates.

Reaction pressures in the alkylation reaction zone may range from pressures sufficient to maintain reactants in the liquid phase to about 1.5 MPa (g). Reactant hydrocarbons may be normally gaseous at alkylation reaction temperatures. Reaction pressures in the range of from about 276 kPa (g) (40 psig) to about 1.1 MPa (g) (160 psig) are suitable. With all reactants in the liquid phase, increased pressure has no significant effect upon the alkylation reaction.

When ionic liquid catalysts are used, the temperature is typically in the range of about −20° C. to the decomposition temperature of the ionic liquid, or about −20° C. to about 100° C., for example. The pressure is typically in the range of atmospheric (0.1 MPa (g)) to about 8.0 MPa (g), or about 0.3 MPa (g) to about 2.5 MPa (g).

Contact times for hydrocarbon reactants in an alkylation reaction zone, in the presence of the alkylation catalyst composition of the present invention generally should be sufficient to provide for essentially complete conversion of olefin reactants in the alkylation zone. Preferably, the contact time is in the range of from about 0.05 minute to about 60 minutes.

The heat generated by the reaction can be eliminated using any of the means known to the skilled person.

The alkylation reaction produces an alkylation reaction mixture typically containing alkylate product containing primarily $C_7$-$C_9$ paraffins along with smaller amounts of $C_5$ and $C_6$ products, $C_{3-}$ products, and $C_{9+}$ paraffins, as well as unreacted iso-$C_4$ paraffins.

The alkylation effluent 135 contains the alkylate products, unreacted feed, and other products.

The disproportionation effluent 115 and the alkylation effluent 135 are combined into combined effluent stream 140 and sent to separation zone 145. Typically, the combined effluent stream 140 is separated into at least an alkylate-rich stream 150, a stream 155 rich in unreacted iso-$C_4$ from the alkylation reaction zone 130 and iso-$C_4$ product from the disproportionation reaction zone 110, and a stream 160 rich in unreacted n-$C_5$ and iso-$C_5$ product from the disproportionation reaction zone 110, and any iso-$C_5$ and/or n-$C_5$ product formed in the alkylation reaction zone 130. Additional streams could also be formed, including a $C_{3-}$ stream 165. In some embodiments, the alkylate-rich stream 150 includes the $C_{6+}$ products from the alkylation reaction zone 130 and the $C_{6+}$ products from the disproportionation reaction zone 110. Alternatively, a separate stream 170 comprising the $C_6$-$C_7$ products from the alkylation reaction zone 130 and the disproportionation reaction zone 110 could be formed. In this case, the alkylate-rich stream could comprise $C_{8+}$ products from the alkylation reaction zone 130 and the disproportionation reaction zone 110.

The separation zone 145 can be any suitable separation zone, such as a fractionation column. If an ionic liquid catalyst is used, the separation zone 145 may include a gravity settler upstream of the fractionation column to remove the ionic liquid.

The alkylate-rich stream 150 (with or without the $C_6$-$C_7$ products from alkylation reaction zone 130 and the disproportionation reaction zone 110) can be blended with gasoline.

The stream 155 rich in unreacted iso-$C_4$ and iso-$C_4$ product can be mixed with make-up iso-$C_4$ 175 to form iso-$C_4$ stream 125 and recycled to the alkylation reaction zone 130 to increase the conversion. Alternatively, make-up iso-$C_4$ stream could be introduced into the alkylation reaction zone 130 directly.

The stream 160 rich in unreacted n-$C_5$ and n-$C_5$ product, and optionally unreacted n-$C_4$ and any i-$C_5$ can be recycled to the disproportionation reaction zone 110.

The $C_{3-}$ stream 165 can be used as feed for a steam cracker, steam reformer, dehydrogenation reactor, oxidative dehydrogenation reactor, or used as fuel gas.

The stream 170 comprising the $C_6$-$C_7$ products from the disproportionation reaction zone 110 and the alkylation reaction zone 130 could be recovered, or could be used as feed for a reformer.

The integrated process may be carried out either as a batch, semi-batch, or continuous type of operation, although, it is preferred for economic reasons to carry out the process continuously. It has been generally established that in disproportionation and alkylation processes, the more intimate the contact between the feedstock and catalyst, the better the quality of disproportionation and alkylate product obtained. With this in mind, the present process, when operated as a batch operation with a liquid catalyst, is characterized by the use of vigorous mechanical stirring or shaking of the reactants and catalysts.

In continuous operations, in one embodiment, reactants may be maintained at sufficient pressures and temperatures to maintain them substantially in the liquid phase and then continuously forced through dispersion devices into the disproportionation and/or alkylation reaction zones. The dispersion devices can be jets, nozzles, porous thimbles, and the like. The reactants are subsequently mixed with the catalyst by conventional mixing means such as mechanical agitators or turbulence or other general means in the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

When the disproportionation catalyst is a liquid catalyst, such as hydrofluoric acid or an ionic liquid, the volume ratio of the hydrofluoric acid or the ionic liquid to the feed in the disproportionation reaction zone is typically less than 1:2. When the alkylation catalyst is a liquid catalyst, the volume ratio of the hydrofluoric acid or the ionic liquid to the iso-$C_4$ hydrocarbon stream and the olefin feed stream in the alkylation reaction is less than 1:2.

Suitable ranges can include from about 1:2 to about 1:100, or about 1:2 to about 1:75, or from about 1:2 to about 1:50, or from about 1:2 to about 1:25, or from about 1:2 to about 1:10, or from about 1:2 to about 1:5.

Figure 2:
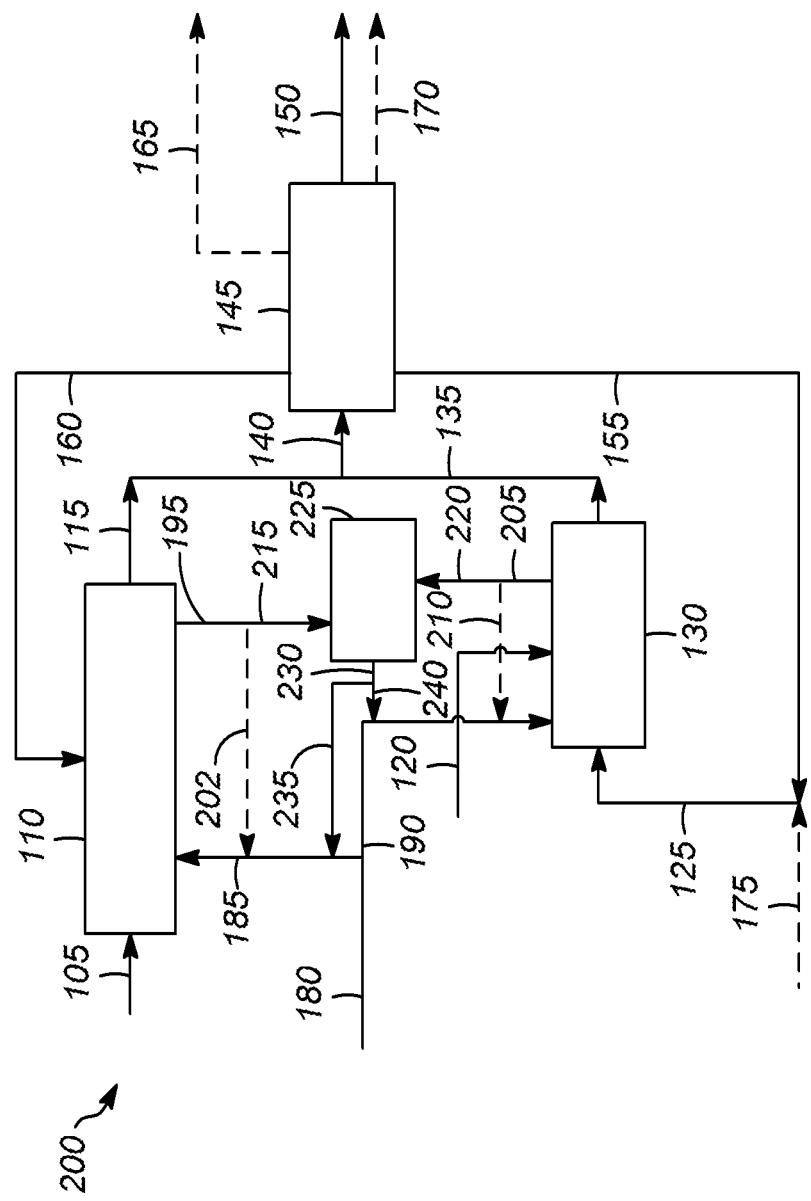
FIG. 2 is an illustration of another embodiment of a process according to the present invention.

FIG. 2 illustrates one embodiment of a process 200 involving the use of an acidic ionic liquid catalyst, with like reference numbers referring to like components.

By acidic ionic liquid, we mean an ionic liquid capable of catalyzing reactions typically carried out with an acid. As known in the art, acids such as sulfuric acid and hydrofluoric acid are often used to catalyze these reactions. These reactions include, e.g. alkylation, oligomerization, isomerization, disproportionation, and reverse disproportionation. Oftentimes the acids employed in these reactions have Hammett acidity functions ($H_0$) less than 7, or less than 5, or less than 3, or less than 0, or less than −3, or less than −5, or less than −7, or less than −9. If the ionic liquid does not possess an acidic proton in its structure (e.g. 1-butyl-3-methylimidazolium heptachloroaluminate), addition of an exogenous acid is acceptable, provided the Hammett acidity function ($H_0$) of the added acid is less than 7 within the ionic liquid, or less than 5, or less than 3, or less than 0, or less than −3, or less than −5, or less than −7, or less than −9. Acidic chloroaluminate-containing ionic liquids have a molar ratio of Al to cation greater than 1.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

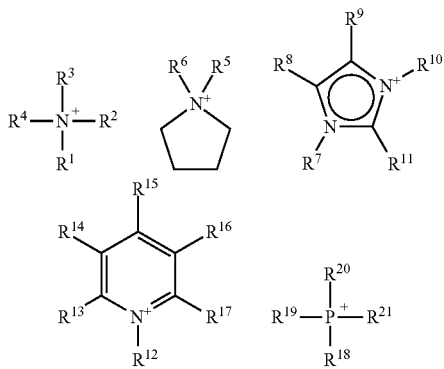

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable. Lactamium based ionic liquids can also be used, such as those described in U.S. Pat. No. 8,709,236, U.S. application Ser. No. 14/271,308, entitled Synthesis of Lactam Based Ionic Liquids, filed May 6, 2014, and U.S. application Ser. No. 14/271,319, entitled Synthesis of N-Alkyl Lactam Based Ionic Liquids, filed May 6, 2014, each of which is incorporated herein by reference.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

A stream of fresh ionic liquid catalyst 180 is divided into stream 185 which is supplied to the disproportionation reaction zone 110 and stream 190 which is supplied to alkylation reaction zone 130.

A stream of used ionic liquid 195 is removed from the disproportionation reaction zone 110. All or a portion 202 of the stream of used ionic liquid can be recycled to the disproportionation reaction zone 110. Similarly, a stream 205 of used ionic liquid is removed from the alkylation reaction zone 130, and all or a portion 210 can be recycled to the alkylation reaction zone.

Over time, when an ionic liquid catalyst is used in hydrocarbon conversion processes, such as disproportionation and alkylation, conjunct polymer forms. By conjunct polymer, we mean the olefinic, conjugated cyclic hydrocarbons that form as a byproduct of various hydrocarbon conversion processes. The ionic liquid catalyst loses its effectiveness over time as the amount of conjunct polymer increases. When the level of conjunct polymer in the ionic liquid becomes too high, the ionic liquid catalyst is said to be spent, and it must either be replaced or regenerated. Various methods for regenerating ionic liquids have been developed, as described below.

All or a portion 215 of the stream of used ionic liquid 195 from the disproportionation reaction zone 110, and all or a portion 220 of stream 205 of used ionic liquid from the alkylation reaction zone 130 are sent to a regeneration zone 225. Various methods of regenerating ionic liquids are known, as described below.

The regenerated ionic liquid stream 230 is split into two portions, with portion 235 being recycled to the disproportionation reaction zone 110, and portion 240 being recycled to the alkylation reaction zone 130.

Figure 3:
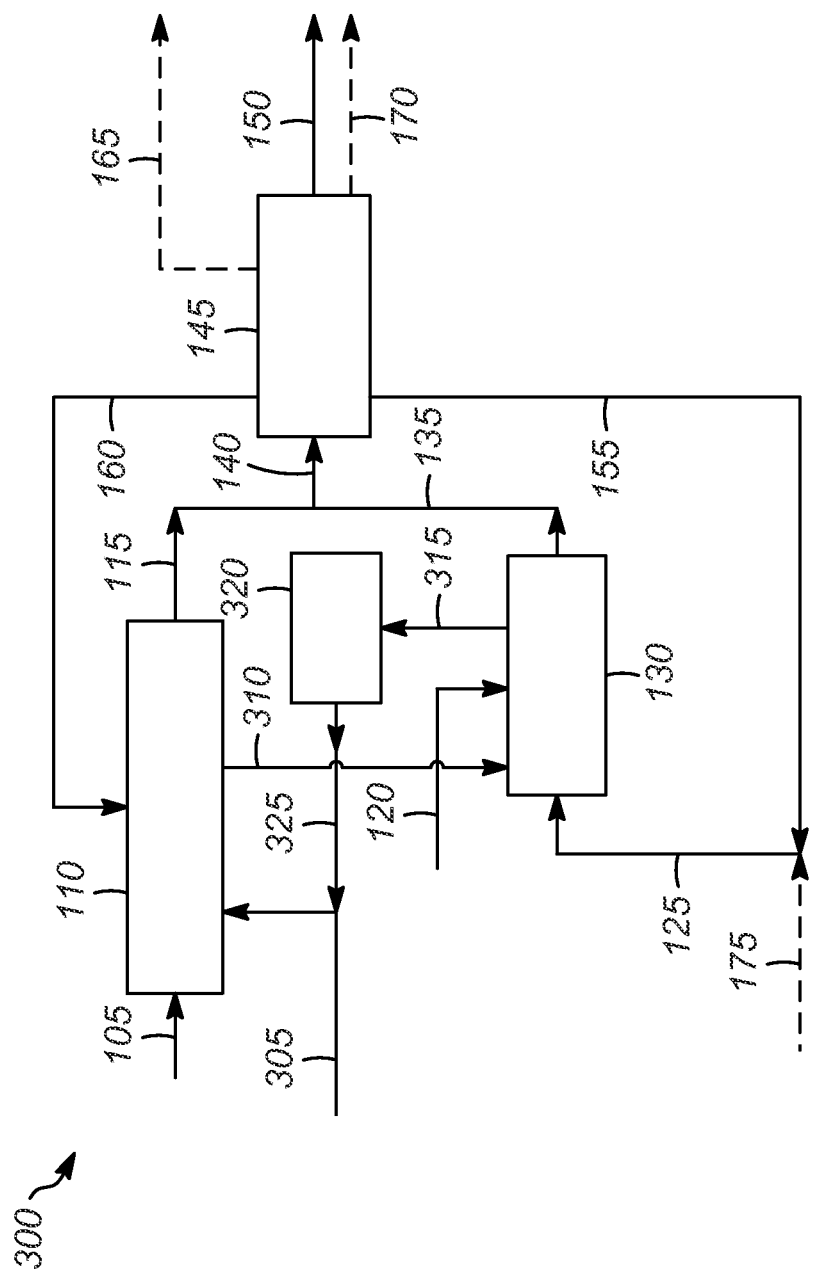
FIG. 3 is an illustration of still another embodiment of a process according to the present invention.

FIG. 3 illustrates another embodiment of the process 300 involving the use of an ionic liquid catalyst, with like reference numbers referring to like components.

A stream of fresh ionic liquid catalyst 305 is supplied to the disproportionation reaction zone 110. A stream of used ionic liquid 310 is removed from the disproportionation reaction zone 110, and all or a portion of the stream of used ionic liquid 310 is sent to the alkylation reaction zone 130. A stream of used ionic liquid 315 is removed from the alkylation reaction zone 130, and all or a portion of the stream of used ionic liquid 315 is sent to the regeneration zone 320. The regenerated ionic liquid stream 325 is recycled to the disproportionation reaction zone 110.

Suitable methods for regenerating ionic liquids include, but are not limited to the following. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. Nos. 7,651,970; 7,825,055; 7,956,002; and 7,732,363.

Another method involves contacting the ionic liquid containing the conjunct polymer with a reducing metal (e.g., Al) in the presence of an inert hydrocarbon (e.g. hexane), but in the absence of added hydrogen, and heating to about 100° C. The conjunct polymer will be transferred to the hydrocarbon phase, allowing for the conjunct polymer to be removed from the ionic liquid phase. See e.g., U.S. Pat. No. 7,674,739.

Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the conjunct polymer to be removed from the IL phase. See e.g., U.S. Pat. No. 7,727,925.

The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727.

Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740.

The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771.

Still another method involves adding a basic reagent that displaces the conjunct polymer and is a part of the regeneration of the catalyst. The basic reagents are described as nitrogen-containing compounds such as amines, pyridinium compounds, or pyrrolidinium compounds. For example, a suitable substrate (e.g. pyridine) is added to the ionic liquid containing the conjunct polymer. After a period of time, an inert hydrocarbon would be added to wash away the liberated conjunct polymer. The ionic liquid precursor [butylpyridinium][Cl] would be added to the ionic liquid (e.g. [butylpyridinium][$Al_2Cl_7$]) containing the conjunct polymer followed by an inert hydrocarbon. After a given time of mixing, the hydrocarbon layer would be separated, resulting in a regenerated ionic liquid. The solid residue would be converted to catalytically active ionic liquid by adding $AlCl_3$. See e.g., U.S. Pat. Nos. 7,737,363 and 7,737,067.

Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623.

Still other methods include contacting the ionic liquid containing the conjunct polymer with an aromatic compound as described in U.S. application Ser. No. 14/229,290, entitled REGENERATION OF AN ACIDIC CATALYST BY ALKYLATION OF AROMATIC COMPOUNDS, filed Mar. 28, 2014; with a Brønsted acid as described in U.S. application Ser. No. 14/229,329, entitled REGENERATION OF AN ACIDIC IONIC LIQUID CATALYST BY ADDITION OF BRØNSTED ACIDS, filed Mar. 28, 2014; with silane compounds as described in U.S. application Ser. No. 14/269,943, entitled REGENERATION OF AN ACIDIC CATALYST BY SILANE ADDITION, filed May 5, 2014; with borane compounds as described in U.S. application Ser. No. 14/269,978, entitled REGENERATION OF AN ACIDIC CATALYST BY BORANE ADDITION, filed May 5, 2014; and with metal complexes as described in U.S. application Ser. No. 14/547,627, entitled REGENERATION OF AN IONIC LIQUID CATALYST USING METAL COMPLEXES, filed Nov. 19, 2014.

EXAMPLES

Example 1

Solid Acid Catalyst

The catalyst was a chlorided alumina catalyst containing platinum made for example by U.S. Pat. No. 5,004,859. The concentration of platinum was in the range of 0.002 wt. % to 2 wt. %, the chloride concentration was in the range of 0.1 to 10 wt. % and the alumina phase was one of alpha, gamma, eta, or theta.

Example 2

Experimental Set Up for Solid Acid Catalyst

The catalytic reactions were typically run using a 7/8" inner diameter stainless steel tube reactor. Prior to catalyst loading, the reactor was dried by heating the reactor to at least 150° C. with a three-zone clam shell furnace under a stream of flowing nitrogen for at least four hours. After the drying procedure was completed, the reactor was cooled to ambient temperature, connected to a nitrogen line, and the reactor opened under flowing nitrogen. The reactor was inserted through a hole in a nitrogen glovebag, and the connection of the glovebag with the reactor was sealed with electrical tape. The top of the open reactor was enclosed within a glovebag and had nitrogen blowing through it. The catalyst from Example 1 was loaded under nitrogen in the glovebag to the reactor under this positive flow of nitrogen. The reactor was sand packed with 50-70 mesh sand, the sand having been previously calcined to 700° C. for 7 h. Typically, 40 ccs of catalyst was loaded into the reactor, and the reaction was run downflow. The feed had a 1.4 MPa(g) (210 psig) hydrogen header and the concentration of dissolved hydrogen in the feed was determined from the literature values reported in the IUPAC Solubility Data Series volumes 5/6 "Hydrogen and Deuterium" (1981) for pentane and butane. It was assumed that the value for pentane would remain constant for the $iC_5$, $iC_5/nC_5$, and $iC_5/nC_5$/cyclopentane (CP) feeds. The feed was passed through a high surface sodium dryer prior to introduction to the reactor and was added to the reactor using a pump. A second pump controlled the chloride addition rate. The chloride was dissolved in the feed, and the chloride source (2-chlorobutane) had previously been dried with activated 3A molecular sieves. The two feed streams were introduced to the reactor by joining the two separate feed streams with a Tee connector immediately prior to their introduction to the reactor. The temperature was measured using K-type thermocouples, and the pressure was controlled by means of a backpressure regulator. The effluent was sent directly to an Agilent 6890N gas chromatograph (GC), and the product was analyzed by means of flame ionization detection. A 60 m, 0.32 mm inner diameter, 1.0 um film thickness DB-1 column was used. The initial oven temperature was 40° C., with a 4 minute hold time at this temperature. The oven was then ramped to 135° C. at a 5° C./min ramp rate, and the program was completed once this temperature was reached. The GC inlet was 250° C. with a hydrogen carrier gas. The product was then sent directly to a product charger and collected.

Example 3

Disproportionation of $iC_5$ Using Solid Acid Catalyst

The catalytic reaction was run according to the procedure outlined above. The conditions and results are listed in Table 1 below and demonstrate that the presence of small amounts of hydrogen increase the stability of the catalyst.

TABLE 1

| Disproportionation of $iC_5$ | | | |
|---|---|---|---|
| TOS (h) | 15 | 20 | 25 |
| T (° C.) | 172 | 172 | 172 |
| P (psig) | 608 | 610 | 611 |
| Cl (ppm) | 1600 | 1600 | 1600 |
| LHSV ($hr^{-1}$) | 1.0 | 1.0 | 1.0 |
| $H_2/HC^a$ | 0.02 | 0.02 | 0.02 |
| $H_2/Cl^b$ | 5 | 5 | 5 |
| % $iC_5$ Conv.$^c$ | 52 | 53 | 54 |
| % $C_5P$ Conv.$^d$ | 41 | 42 | 42 |
| % Selec. Disp.$^e$ | 80 | 80 | 77 |
| Compound | | | |
| Methane | 0.00 | 0.00 | 0.00 |
| Ethane | 0.00 | 0.00 | 0.00 |
| Propane | 0.53 | 0.62 | 0.63 |
| $iC_4$ | 21.07 | 21.67 | 20.18 |
| $nC_4$ | 2.54 | 2.54 | 2.51 |
| $iC_5$ | 48.28 | 47.06 | 45.62 |
| $nC_5$ | 10.51 | 10.89 | 12.36 |
| 22DMB | 1.06 | 1.08 | 1.34 |
| 23DMB | 1.77 | 1.75 | 1.79 |
| 2MP | 5.81 | 5.73 | 5.91 |
| 3MP | 3.45 | 3.41 | 3.55 |
| $nC_6$ | 1.49 | 1.47 | 1.63 |
| $C_7P$ | 2.32 | 2.42 | 2.45 |
| $C_8+$ | 1.17 | 1.37 | 1.40 |
| Unknown | 0.00 | 0.00 | 0.00 |

$^a$Molar ratio of hydrogen to hydrocarbon in feed,
$^b$molar ratio of hydrogen to chloride,
$^c$% $iC_5$ Conv. = 100 − wt. % $iC_5$,
$^d$% $C_5P$ Conv. = 100 − wt. % $iC_5$ − wt. % $nC_5$ and
$^e$% Selec. Disp. = (wt. % $C_{4-}$ + wt. % $C_{6+}$)/(100 − wt. % $iC_5$) × 100.

Example 4

Disproportionation of $nC_5$ Using Solid Acid Catalyst

The catalytic reaction was run according to the procedure outlined above. The conditions and results are listed in Table 2 below and demonstrate that the disproportionation of $nC_5$ readily occurs with these types of catalysts and that with small amounts of hydrogen being present, the catalyst stability is increased.

TABLE 2

| Disproportionation of $nC_5$ | | | |
|---|---|---|---|
| TOS (h) | 8 | 13 | 28 |
| T (° C.) | 176 | 175 | 171 |
| P (psig) | 619 | 618 | 622 |
| Cl (ppm) | 1600 | 1600 | 1600 |
| LHSV ($hr^{-1}$) | 1.0 | 1.0 | 1.0 |
| $H_2/HC^a$ | 0.02 | 0.02 | 0.02 |
| $H_2/Cl^b$ | 5 | 5 | 5 |
| % $nC_5$ Conv.$^c$ | 69 | 68 | 67 |
| % $C_5P$ Conv.$^d$ | 35 | 35 | 33 |
| % Selec. Disp.$^e$ | 50 | 52 | 50 |
| Compound | | | |
| Methane | 0.00 | 0.00 | 0.00 |
| Ethane | 0.00 | 0.00 | 0.00 |
| Propane | 0.81 | 0.81 | 0.66 |
| $iC_4$ | 15.49 | 15.83 | 15.19 |
| $nC_4$ | 3.70 | 3.32 | 2.54 |
| $iC_5$ | 34.05 | 32.70 | 33.60 |
| $nC_5$ | 31.26 | 32.06 | 33.18 |
| 22DMB | 1.47 | 1.35 | 1.33 |
| 23DMB | 1.30 | 1.36 | 1.37 |
| 2MP | 4.09 | 4.25 | 4.25 |
| 3MP | 2.54 | 2.64 | 2.62 |
| $nC_6$ | 1.44 | 1.45 | 1.32 |
| $C_7P$ | 2.46 | 2.64 | 2.44 |
| $C_8+$ | 1.39 | 1.60 | 1.50 |
| Unknown | 0.00 | 0.00 | 0.00 |

$^a$Molar ratio of hydrogen to hydrocarbon in feed,
$^b$molar ratio of hydrogen to chloride,
$^c$% $nC_5$ Conv. = 100 − wt. % $nC_5$,
$^d$% $C_5P$ Conv. = 100 − wt. % $iC_5$ − wt. % $nC_5$ and
$^e$% Selec. Disp. = (wt. % $C_{4-}$ + wt. % $C_{6+}$)/(100 − wt. % $nC_5$) × 100.

Example 5

Experimental Set Up for Ionic Liquid Reactions

The set-up included a 300 mL autoclave equipped with a mechanical stirrer, pressure gauge, thermocouple, dipleg, rupture disc, and valves to introduce the feed and withdraw an aliquot for GC analysis. The rupture disc vented to a knock out pot. The house nitrogen passed through a pressure regulator to a high surface sodium column and was then split: feeding to the charger for feed introduction or to a line for various uses (i.e., 2-methyl-2-chloropropane/$C_5P$ introduction). The dipleg was constructed such that the height positions it in the paraffin layer. Upon opening the valve, the withdrawn paraffin layer passed through a column of silica, to the GC valve and then through a metering valve into a waste container. The reaction mixture was analyzed using the ASTM UOP690-99 method.

Example 6

Synthesis of [1-butyl-1-methylpyrrolidinium] [$Al_2Cl_7$]

An oven-dried round bottom flask was charged with [1-butyl-1-methylpyrrolidinium][Cl]. The material was attached to a rotary evaporator, dried under vacuum at 110° C. for at least 14 h, and then sealed under vacuum with a connecting adapter.

The dried [1-butyl-1-methylpyrrolidinium][Cl] was immediately brought into a nitrogen glovebox and stored there. A synthesis was achieved by massing 57.14 g (322 mmol) of [1-butyl-1-methylpyrrolidinium][Cl] into an oven-dried flask equipped with a stir bar in the nitrogen glovebox. To this was added 83.93 g (629 mmol) of $AlCl_3$ at ambient temperature and the mixture stirred. The solids reacted to produce a homogenous liquid.

Example 7

$nC_5$ with [1-butyl-1-methylpyrrolidinium][$Al_2Cl_7$] at 95° C.

A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 52.795 g of [1-butyl-1-methylpyrrolidinium][$Al_2Cl_7$] and the autoclave head was attached. To the sample cylinder 5.24 g of 2-chloro-2-methylpropane, which had previously been dried over activated sieves, was added. The sample cylinder was closed under nitrogen, and both the autoclave and sample cylinder were removed from the glovebox. The autoclave was charged with 98 g of n-pentane from a pressurized feed charger without displacing the nitrogen present in the autoclave. The n-pentane passed over a high surface sodium column to remove any water before entering the autoclave. Similarly, the nitrogen used to pressurize the charger and for all other work passed over a separate high surface sodium column. The sample cylinder was charged with 33 g of n-pentane using the same method described above and attached to the autoclave. The autoclave was heated to 95° C., and the 2-chloro-2-methylpropane/n-pentane solution in the sample cylinder was added with an over-pressure of nitrogen. After complete addition, the initial pressure in the autoclave was 260 psi (1.793 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a Sift column, and then passing it directly into a GC sample loop. The results of the run are shown in Tables 3.

TABLE 3

Disproportionation and Isomerization of n-Pentane at 95° C. with [1-butyl-1-methylpyrrolidinium] [$Al_2Cl_7$], wt. % of reaction mixture

| t (h) | % Conv. | $C_3-$ | $iC_4$ | $nC_4$ | $iC_5$ | $nC_5$ | $C_6P$ | $C_7+$ |
|---|---|---|---|---|---|---|---|---|
| 0.6 | 57 | 0.49 | 18.16 | 2.44 | 18.55 | 42.87 | 10.02 | 7.48 |
| 1.9 | 84 | 1.22 | 28.59 | 5.73 | 22.01 | 15.60 | 14.75 | 12.00 |
| 3.2 | 89 | 1.70 | 30.42 | 7.70 | 21.66 | 10.57 | 15.38 | 12.54 |
| 4.4 | 91 | 1.96 | 30.79 | 8.72 | 21.31 | 9.06 | 15.51 | 12.65 |

Example 8

Synthesis of [tributyl(hexyl)phosphonium] [$Al_2Cl_6Br$] ([($"Bu$)_3P(Hex)$][$Al_2Cl_6Br$])

An oven-dried round bottom flask was charged with tributyl(hexyl)phosphonium bromide ([($"Bu$)_3P(Hex)$][Br]).

The material was attached to a rotary evaporator and dried under vacuum at 110° C. for at least 14 h. The dried [($"Bu$)_3P(Hex)$][Br] was immediately brought into a nitrogen glovebox and stored there. A synthesis was achieved by massing 17.589 g (47.88 mmol) of [($"Bu$)_3P(Hex)$][Br] into an oven-dried flask equipped with a stir bar in the nitrogen glovebox. To this was added 12.775 g (95.81 mmol) of $AlCl_3$ at ambient temperature. The mixture was stirred, and the solids slowly reacted over the course of one week to produce a homogenous pale-yellow liquid.

Example 9 nC5 with [($"Bu$)_3P(Hex)$][$Al_2Cl_6Br$] at 95° C. in a Hastelloy C Autoclave

A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.409 g of [($"Bu$)_3P(Hex)$][$Al_2Cl_6Br$], and the autoclave head was attached. 3.679 g of 2-chloro-2-methylpropane, which had previously been dried over activated sieves, was added to the sample cylinder. The sample cylinder was closed under nitrogen, and both the autoclave and sample cylinder were removed from the glovebox. The autoclave was charged with 102 g of n-pentane from a pressurized feed charger without displacing the nitrogen present in the autoclave. The n-pentane passed over a high surface sodium column to remove any water before entering the autoclave. Similarly, the nitrogen used to pressurize the charger and for all other work passed over a separate high surface sodium column. The sample cylinder was charged with 15 g of n-pentane using the same method described above and then attached to the autoclave. The autoclave was heated to 95° C., and the 2-chloro-2-methylpropane/n-pentane solution in the sample cylinder was added with an over-pressure of nitrogen. After complete addition, the initial pressure in the autoclave was 1.1 MPa (160 psig), and the autoclave was then set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a Sift column, and then passing it directly into a GC sample loop. The results of the run are shown in Table 4.

TABLE 4

Disproportionation and Isomerization of n-Pentane at 95° C., wt. % of reaction mixture

| t (h) | % Conv. | $C_3-$ | $iC_4$ | $nC_4$ | $iC_5$ | $nC_5$ | $C_6P$ | $C_7+$ |
|---|---|---|---|---|---|---|---|---|
| 1.0 | 59 | 0.42 | 18.63 | 1.71 | 19.46 | 41.34 | 10.27 | 8.14 |
| 2.2 | 70 | 0.94 | 22.7 | 3.08 | 20.83 | 29.43 | 12.54 | 10.30 |
| 3.5 | 76 | 0.91 | 25.1 | 4.06 | 21.56 | 23.72 | 13.57 | 11.03 |
| 4.8 | 80 | 1.05 | 26.39 | 4.78 | 21.83 | 20.06 | 14.26 | 11.63 |
| 8.0 | 85 | 1.35 | 27.64 | 6.10 | 21.68 | 14.82 | 14.78 | 12.84 |

Example 10

Preparation of Tributylhexylphosphonium Chloroaluminate Ionic Liquid

Tributylhexylphosphonium chloroaluminate is a room temperature ionic liquid prepared by mixing anhydrous tributylhexylphosphonium chloride with slow addition of 2 moles of anhydrous aluminum chloride in an inert atmosphere. After several hours of mixing, a pale yellow liquid was obtained. The resulting acidic IL was used in the following example.

Example 11

Alkylation of Isobutane with 2-Butene using Tributylhexylphosphonium Chloroaluminate Ionic Liquid Catalyst Alkylation of isobutane with 2-butene was carried out in a 300 cc continuously stirred autoclave. 8 grams of tributylhexylphosphonium heptachloroaluminate (TBHP)-$Al_2Cl_7$ ionic liquid and 0.438 g of 2-chlorobutane were added to the autoclave in a glovebox to avoid exposure to moisture. 80 g of isobutane were then charged and the autoclave was pressured to 3.4 MPa (g) (500 psig) with nitrogen. Stirring was started at 1900 rpm. 7.67 grams of olefin feed (2-butene feed to which 10% n-pentane tracer had been added) was then charged into the autoclave at a rate of 107.8 mL olefin/hour for 8 minutes. Stirring was stopped, and the ionic liquid and hydrocarbon phases were allowed to settle for 30 seconds. The hydrocarbon phase was then analysed by GC. For this example, the autoclave temperature was maintained at 25° C.

TABLE 5

Alkylation with Tributylhexylphosphonium Chloroaluminate Ionic Liquid Catalyst

| | |
|---|---|
| Olefin Conversion, wt % | 100 |
| $C_{5+}$ Yield, wt. alkylate/wt olefin | 2.10 |
| $C_{5+}$ Alkylate RONC | 96.0 |
| $C_5$-$C_7$ Selectivity, wt % | 15 |
| $C_8$ Selectivity, wt % | 77 |
| $C_{9+}$ Selectivity, wt % | 8 |
| TMP/DMH | 14.8 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An integrated process comprising:
   introducing a feed comprising n-$C_5$ hydrocarbons to a disproportionation reaction zone in the presence of an ionic liquid disproportionation catalyst comprising an ionic liquid, wherein the ionic liquid is homogeneous and unsupported, under disproportionation reaction conditions to form a disproportionation mixture comprising iso-$C_4$ and $C_{6+}$ disproportionation products and unreacted n-$C_5$ hydrocarbons;
   introducing an iso-$C_4$ hydrocarbon stream and an olefin feed stream comprising at least one of ethylene, propylene, and butenes into an alkylation reaction zone in the presence of an ionic liquid alkylation catalyst comprising an ionic liquid under alkylation reaction conditions to produce an alkylation mixture comprising alkylate products and unreacted iso-$C_4$ paraffins;
   combining the disproportionation mixture and the alkylation mixture to form a combined mixture;
   separating the combined mixture into at least a stream comprising the alkylate products, an iso-$C_4$ stream comprising the iso-$C_4$ disproportionation products and the unreacted iso-$C_4$ paraffins, and a stream comprising the unreacted n-$C_5$ hydrocarbons;
   recycling the iso-$C_4$ stream to the alkylation reaction zone wherein the iso-$C_4$ stream comprises the iso-$C_4$ hydrocarbon stream;
   recycling the stream comprising the unreacted n-$C_5$ hydrocarbons to the disproportionation reaction zone;
   recovering the stream comprising the alkylate products;
   introducing fresh ionic liquid disproportionation catalyst and fresh ionic liquid alkylation catalyst into the disproportionation reaction zone and the alkylation reaction zone, respectively;
   removing used ionic liquid disproportionation catalyst and used ionic liquid alkylation catalyst from the disproportionation reaction zone and the alkylation reaction zone, respectively;
   regenerating at least a portion of (i) the used ionic liquid disproportionation catalyst and (ii) the used ionic liquid alkylation catalyst in a regeneration zone to produce a regenerated ionic liquid catalyst; and
   recycling a first portion of the regenerated ionic liquid catalyst to the disproportionation reaction zone and recycling a second portion of the regenerated ionic liquid catalyst to the alkylation reaction zone.

2. The process of claim 1 wherein the stream comprising the alkylate product further comprises the $C_{6+}$ disproportionation products.

3. The process of claim 1 wherein at least one of the disproportionation mixture and the alkylation mixture further comprises $C_{3-}$ hydrocarbons and wherein separating the combined mixture into at least the stream comprising the alkylate products, the iso-$C_4$ stream comprising the iso-$C_4$ disproportionation products and the unreacted iso-$C_4$ paraffins, and the stream comprising the unreacted n-$C_5$ hydrocarbons comprises separating the combined mixture into at least the stream comprising the alkylate products, the iso-$C_4$ stream comprising the iso-$C_4$ disproportionation products and the unreacted iso-$C_4$ paraffins, the stream comprising the unreacted n-$C_5$ hydrocarbons, and a stream comprising the $C_{3-}$ hydrocarbons.

4. The process of claim 1 further comprising introducing a make-up stream comprising iso-$C_4$ hydrocarbons into the alkylation reaction zone.

5. The process of claim 1 wherein introducing the feed comprising the n-$C_5$ hydrocarbons to the disproportionation reaction zone in the presence of the ionic liquid disproportionation catalyst comprises introducing the feed comprising the n-$C_5$ hydrocarbons to the disproportionation reaction zone in the presence of the ionic liquid disproportionation catalyst and an acid or a carbocation promoter.

6. The process of claim 1 wherein at least one of a volume ratio of the ionic liquid disproportionation catalyst to the feed in the disproportionation reaction zone or a volume ratio of the ionic liquid alkylation catalyst to the iso-$C_4$ hydrocarbon stream and the olefin feed stream is less than 1:2.

7. The process of claim 1 wherein introducing the fresh ionic liquid disproportionation catalyst and fresh ionic liquid alkylation catalyst into the disproportionation reaction zone and the alkylation reaction zone, respectively, comprises introducing the same fresh ionic liquid catalyst into the disproportionation reaction zone and the alkylation reaction zone.

8. The process of claim 1 wherein the regeneration zone comprises a first regeneration zone and a second regeneration zone and wherein the ionic liquid disproportionation catalyst and the ionic liquid alkylation catalyst are different, and:
   wherein regenerating at least the portion of (i) the used ionic liquid disproportionation catalyst and (ii) the used ionic liquid alkylation catalyst in the regeneration zone comprises:
      regenerating at least a portion of the used ionic liquid disproportionation catalyst in the first regeneration zone to produce a regenerated ionic liquid disproportionation catalyst;
      regenerating at least a portion of the used ionic liquid alkylation catalyst in the second regeneration zone to produce a regenerated ionic liquid alkylation catalyst; and
   wherein recycling a first portion of the regenerated ionic liquid catalyst to the disproportionation reaction zone and recycling a second portion of the regenerated ionic liquid catalyst to the alkylation reaction zone comprises:
      recycling the regenerated ionic liquid disproportionation catalyst to the disproportionation reaction zone; and
      recycling the regenerated ionic liquid alkylation catalyst to the alkylation reaction zone.

9. An integrated process comprising:
   introducing a feed comprising n-$C_5$ hydrocarbons to a disproportionation reaction zone in the presence of an ionic liquid disproportionation catalyst comprising an ionic liquid, wherein the ionic liquid is homogeneous and unsupported, under disproportionation reaction conditions to form a disproportionation mixture comprising iso-$C_4$ and $C_{6+}$ disproportionation products and unreacted n-$C_5$ hydrocarbons;
   introducing an iso-$C_4$ hydrocarbon stream and an olefin feed stream comprising at least one of ethylene, propylene, and butenes into an all reaction zone in the presence of an ionic liquid alkylation catalyst comprising an ionic liquid under alkylation reaction conditions to produce an alkylation mixture comprising alkylate products and unreacted iso-$C_4$ paraffins;
   combining the disproportionation mixture and the alkylation mixture to form a combined mixture;
   separating the combined mixture into at least a stream comprising the alkylate products and the $C_{6+}$ disproportionation products, an iso-$C_4$ stream comprising the iso-$C_4$ disproportionation products and the unreacted iso-$C_4$ paraffins, and a stream comprising the unreacted n-$C_5$ hydrocarbons;
   recycling the iso-$C_4$ stream to the alkylation reaction zone wherein the iso-$C_4$ stream comprises the iso-$C_4$ hydrocarbon stream;
   recycling the stream comprising the unreacted n-$C_5$ hydrocarbons to the disproportionation reaction zone;
   recovering the stream comprising the alkylate products and the $C_{6+}$ disproportionation products;
   introducing fresh ionic liquid disproportionation catalyst and fresh ionic liquid alkylation catalyst into the disproportionation reaction zone and the alkylation reaction zone, respectively;
   removing used ionic liquid disproportionation catalyst and used ionic liquid alkylation catalyst from the disproportionation reaction zone and the alkylation reaction zone, respectively;
   regenerating at least a portion of (i) the used ionic liquid disproportionation catalyst and (ii) the used ionic liquid alkylation catalyst in a regeneration zone to produce a regenerated ionic liquid catalyst; and
   recycling a first portion of the regenerated ionic liquid catalyst to the disproportionation reaction zone and recycling a second portion of the regenerated ionic liquid catalyst to the alkylation reaction zone.

10. The process of claim 9 wherein at least one of the disproportionation mixture and the alkylation mixture further comprises $C_{3-}$ hydrocarbons and wherein separating the combined mixture into at least the stream comprising the alkylate products and the $C_{6+}$ disproportionation products, the iso-$C_4$ stream comprising the iso-$C_4$ disproportionation products and the unreacted iso-$C_4$ paraffins, and the stream comprising unreacted n-$C_5$ hydrocarbons comprises separating the combined mixture into at least the stream comprising the alkylate products and the $C_{6+}$ disproportionation products, the iso-$C_4$ stream comprising the iso-$C_4$ disproportionation products and the unreacted iso-$C_4$ paraffins, the stream comprising unreacted n-$C_5$ hydrocarbons, and a stream comprising the $C_{3-}$ hydrocarbons.

11. The process of claim 9 wherein introducing the feed comprising the n-$C_5$ hydrocarbons to the disproportionation reaction zone in the presence of the ionic liquid disproportionation catalyst comprises introducing a feed comprising n-$C_4$ and n-$C_5$ hydrocarbons to the disproportionation reaction zone in the presence of the ionic liquid disproportionation catalyst and an acid or a carbocation promoter.

12. The process of claim 9 wherein at least one of a volume ratio of the ionic liquid disproportionation catalyst to the feed in the disproportionation reaction zone or a volume ratio of the ionic liquid alkylation catalyst to the iso-$C_4$ hydrocarbon stream and the olefin feed stream is less than 1:2.

13. The process of claim 9 wherein the regeneration zone comprises a first regeneration zone and a second regeneration zone and wherein the ionic liquid disproportionation catalyst and the ionic liquid alkylation catalyst are different, and:
   wherein regenerating at least a portion of (i) the used ionic liquid disproportionation catalyst and (ii) the used ionic liquid alkylation catalyst in a regeneration zone to produce a regenerated ionic liquid catalyst comprises:
      regenerating at least a portion of the used ionic liquid disproportionation catalyst in the first regeneration zone to produce a regenerated ionic liquid disproportionation catalyst;
      regenerating at least a portion of the used ionic liquid alkylation catalyst in the second regeneration zone to produce a regenerated ionic liquid alkylation catalyst; and
   wherein recycling the first portion of the regenerated ionic liquid catalyst to the disproportionation reaction zone and recycling the second portion of the regenerated ionic liquid catalyst to the alkylation reaction zone comprises:
      recycling the regenerated ionic liquid disproportionation catalyst to the disproportionation reaction zone; and
      recycling the regenerated ionic liquid alkylation catalyst to the alkylation reaction zone.

14. An integrated process comprising:

introducing a feed comprising n-$C_5$ hydrocarbons to a disproportionation reaction zone in the presence of an ionic liquid disproportionation catalyst comprising an ionic liquid, wherein the ionic liquid is homogeneous and unsupported, under disproportionation reaction conditions to form a disproportionation mixture comprising iso-$C_4$ and $C_{6+}$ disproportionation products and unreacted n-$C_5$ hydrocarbons;

introducing an iso-$C_4$ hydrocarbon stream and an olefin feed stream comprising at least one of ethylene, propylene, and butenes into an all reaction zone in the presence of an ionic liquid alkylation catalyst comprising an ionic liquid under alkylation reaction conditions to produce an alkylation mixture comprising alkylate products and unreacted iso-$C_4$ paraffins;

combining the disproportionation mixture and the alkylation mixture to form a combined mixture;

separating the combined mixture into at least a stream comprising the alkylate products, an iso-$C_4$ stream comprising the iso-$C_4$ disproportionation products and the unreacted iso-$C_4$ paraffins, and a stream comprising the unreacted n-$C_5$ hydrocarbons;

recycling the iso-$C_4$ stream to the alkylation reaction zone wherein the iso-$C_4$ stream comprises the iso-$C_4$ hydrocarbon stream;

recycling the stream comprising the unreacted n-$C_5$ hydrocarbons to the disproportionation reaction zone;

recovering the stream comprising the alkylate products;

introducing fresh ionic liquid disproportionation catalyst into the disproportionation reaction zone;

removing a stream of used ionic liquid disproportionation catalyst from the disproportionation reaction zone after forming the disproportionation mixture introducing at least a portion of the stream of used ionic liquid disproportionation catalyst into the alkylation reaction zone, wherein the at least a portion of the stream of used ionic liquid disproportionation catalyst comprises the ionic liquid alkylation catalyst;

removing a stream of further used ionic liquid alkylation catalyst from the alkylation reaction zone after producing the alkylation mixture;

regenerating at least a portion of the stream of further used ionic liquid alkylation catalyst from the alkylation reaction zone in a regeneration zone to produce a regenerated ionic liquid catalyst; and recycling the regenerated ionic liquid catalyst to the disproportionation reaction zone.

* * * * *